US007163813B2

(12) United States Patent
Cheung

(10) Patent No.: US 7,163,813 B2
(45) Date of Patent: Jan. 16, 2007

(54) BIOLOGICAL COMPOSITIONS AND METHODS FOR TREATMENT OF COLORECTAL CANCER

(75) Inventor: Ling Yuk Cheung, Hong Kong (HK)

(73) Assignee: Ultra Biotech Limited, Douglas (GB)

(*) Notice: Subject to any disclaimer, the term of this patent is extended or adjusted under 35 U.S.C. 154(b) by 0 days.

(21) Appl. No.: 11/226,673

(22) Filed: Sep. 13, 2005

(65) Prior Publication Data

US 2006/0024326 A1   Feb. 2, 2006

Related U.S. Application Data

(62) Division of application No. 10/460,341, filed on Jun. 11, 2003, now Pat. No. 6,987,012.

(51) Int. Cl.
*C12N 13/00* (2006.01)
*A01N 63/04* (2006.01)
*A61K 9/00* (2006.01)
*A61K 47/00* (2006.01)

(52) U.S. Cl. .................... 435/173.1; 424/195.16; 424/400; 424/439

(58) Field of Classification Search ............ 435/173, 435/173.1; 424/195.16, 400, 439
See application file for complete search history.

(56) References Cited

U.S. PATENT DOCUMENTS

| 2,107,830 | A | 2/1938 | Liebesny et al. |
|---|---|---|---|
| 3,711,392 | A | 1/1973 | Metzger |
| 3,870,599 | A | 3/1975 | Azarowicz |
| 3,903,307 | A | 9/1975 | Kimura |
| 3,968,254 | A | 7/1976 | Rhodes et al. |
| 4,041,182 | A | 8/1977 | Erickson et al. |
| 4,055,667 | A | 10/1977 | Linton et al. |
| 4,348,483 | A | 9/1982 | Skogerson |
| 4,582,708 | A | 4/1986 | Tipton et al. |
| 5,082,936 | A | 1/1992 | James et al. |
| 5,504,079 | A | 4/1996 | James et al. |
| 5,578,486 | A | 11/1996 | Zhang |
| 5,624,686 | A | 4/1997 | Shimoda et al. |
| 5,952,020 | A | 9/1999 | Lizak |
| 5,981,219 | A | 11/1999 | Flugge et al. |
| 6,143,731 | A | 11/2000 | James et al. |
| 6,159,510 | A | 12/2000 | Lizak |
| 6,197,295 | B1 | 3/2001 | Hsia et al. |
| 6,214,337 | B1 | 4/2001 | Hayen et al. |
| 6,391,617 | B1 | 5/2002 | Cheung |
| 6,391,618 | B1 | 5/2002 | Cheung |
| 6,391,619 | B1 | 5/2002 | Cheung |
| 6,416,982 | B1 | 7/2002 | Zhang |
| 6,436,695 | B1 | 8/2002 | Cheung |
| 6,440,713 | B1 | 8/2002 | Cheung |
| 6,649,383 | B1 | 11/2003 | Cheung |
| 6,660,508 | B1 | 12/2003 | Cheung |
| 6,709,849 | B1 | 3/2004 | Cheung |
| 6,753,008 | B1 | 6/2004 | Cheung |
| 6,756,050 | B1 | 6/2004 | Cheung |
| 6,759,055 | B1 | 7/2004 | Cheung |
| 6,793,933 | B1 | 9/2004 | Cheung |
| 6,828,131 | B1 | 12/2004 | Zhang |
| 6,914,067 | B1* | 7/2005 | Govindarajan et al. ..... 514/283 |
| 2002/0099026 | A1 | 7/2002 | Goodman et al. |
| 2002/0123127 | A1 | 9/2002 | Cheung |
| 2002/0123129 | A1 | 9/2002 | Cheung |
| 2002/0123130 | A1 | 9/2002 | Cheung |
| 2003/0230126 | A1 | 12/2003 | Cheung |
| 2003/0230245 | A1 | 12/2003 | Cheung |
| 2003/0232038 | A1 | 12/2003 | Cheung |
| 2003/0232039 | A1 | 12/2003 | Cheung |
| 2003/0232059 | A1 | 12/2003 | Cheung |
| 2003/0235565 | A1 | 12/2003 | Cheung |
| 2003/0235566 | A1 | 12/2003 | Cheung |
| 2003/0235567 | A1 | 12/2003 | Cheung |
| 2003/0235568 | A1 | 12/2003 | Cheung |
| 2003/0235569 | A1 | 12/2003 | Cheung |
| 2003/0235570 | A1 | 12/2003 | Cheung |
| 2004/0001812 | A1 | 1/2004 | Cheung |
| 2004/0001813 | A1 | 1/2004 | Cheung |
| 2004/0001814 | A1 | 1/2004 | Cheung |
| 2004/0001857 | A1 | 1/2004 | Cheung |

(Continued)

FOREIGN PATENT DOCUMENTS

CN    1 110 317    10/1995

(Continued)

OTHER PUBLICATIONS

Bassett CA. 1993. Beneficial effects of electromagnetic fields. *J Cell Biochem.* 51(4):387-393.

(Continued)

*Primary Examiner*—Christopher R Tate
*Assistant Examiner*—Randall Winston
(74) *Attorney, Agent, or Firm*—Jones Day

(57) ABSTRACT

The present invention relates to pharmaceutical compositions and dietary supplement comprising yeast cells that can produce a healthful benefit in a subject inflicted with colorectal cancer. The biological compositions can be used to retard the growth of colorectal cancer cells and/or prolonging the time of survival of the subject. The invention also relates to methods for manufacturing the biological compositions.

4 Claims, 2 Drawing Sheets

U.S. PATENT DOCUMENTS

| | | |
|---|---|---|
| 2004/0001859 A1 | 1/2004 | Cheung |
| 2004/0005335 A1 | 1/2004 | Cheung |
| 2004/0005336 A1 | 1/2004 | Cheung |
| 2004/0005680 A1 | 1/2004 | Cheung |
| 2004/0168492 A1 | 9/2004 | Cheung |
| 2004/0253251 A1 | 12/2004 | Cheung |
| 2004/0253252 A1 | 12/2004 | Cheung |
| 2004/0253253 A1 | 12/2004 | Cheung |
| 2004/0253254 A1 | 12/2004 | Cheung |
| 2004/0253255 A1 | 12/2004 | Cheung |
| 2004/0253256 A1 | 12/2004 | Cheung |
| 2004/0253257 A1 | 12/2004 | Cheung |
| 2004/0253258 A1 | 12/2004 | Cheung |
| 2004/0253259 A1 | 12/2004 | Cheung |
| 2004/0253260 A1 | 12/2004 | Cheung |
| 2004/0253261 A1 | 12/2004 | Cheung |
| 2004/0253262 A1 | 12/2004 | Cheung |
| 2004/0253263 A1 | 12/2004 | Cheung |
| 2004/0253264 A1 | 12/2004 | Cheung |
| 2004/0253265 A1 | 12/2004 | Cheung |
| 2004/0253266 A1 | 12/2004 | Cheung |
| 2004/0253267 A1 | 12/2004 | Cheung |
| 2004/0253268 A1 | 12/2004 | Cheung |
| 2004/0265990 A1 | 12/2004 | Cheung |
| 2005/0106166 A1 | 5/2005 | Cheung |
| 2005/0106167 A1 | 5/2005 | Cheung |
| 2005/0106168 A1 | 5/2005 | Cheung |
| 2005/0106169 A1 | 5/2005 | Cheung |
| 2005/0106170 A1 | 5/2005 | Cheung |
| 2005/0106171 A1 | 5/2005 | Cheung |
| 2005/0106172 A1 | 5/2005 | Cheung |
| 2005/0106173 A1 | 5/2005 | Cheung |
| 2005/0106174 A1 | 5/2005 | Cheung |
| 2005/0106704 A1 | 5/2005 | Cheung |
| 2005/0106705 A1 | 5/2005 | Cheung |
| 2005/0150264 A1 | 7/2005 | Cheung |
| 2005/0155400 A1 | 7/2005 | Cheung |

FOREIGN PATENT DOCUMENTS

| | | |
|---|---|---|
| CN | 1 207 873 | 2/1999 |
| EP | 553 377 | 8/1993 |
| ES | 475500 | 11/1978 |
| FR | 2 222 433 | 10/1974 |
| JP | 60 028893 | 2/1985 |
| SU | 1 071 637 | 2/1984 |
| SU | 1 722 364 | 3/1992 |
| SU | 1 750 570 | 7/1992 |
| WO | WO 87/02705 | 5/1987 |
| WO | WO 95/04814 | 2/1995 |
| WO | WO 02/20431 | 3/2002 |
| WO | WO 02/062981 | 8/2002 |
| WO | WO 02/062982 | 8/2002 |
| WO | WO 02/062983 | 8/2002 |
| WO | WO 02/062984 | 8/2002 |
| WO | WO 02/062985 | 8/2002 |
| WO | WO 02/070436 | 9/2002 |
| WO | WO 02/070682 | 9/2002 |
| WO | WO 02/070683 | 9/2002 |

OTHER PUBLICATIONS

Binninger et al. 1997. Effects of 60Hz AC magnetic fields on gene expression following exposure over multiple cell generations using *Saccharomyces cerevisiae. Bioelectrochemistry and Bioenergetics* 43(1):83-89.

Born et al. 1993. *Saccharomyces boulardii* therapy of HIV associated features (2). *Deutsche Medizinische Wochenschrift* (Germany) 118(2):765.

Filho et al. 1998. Dose effect of oral *Saccharomyces boulardii* treatments on morbidity and mortality in immunosuppressed mice. *J Med Microbio.* (United Kingdom) 47(2):111-116.

Gonzalez et al. 1980. Effects of an electric field of sinusoidal waves on the amino acid biosynthesis by *Azotobacter. Z. Naturforsch.* 35c:258-261.

Goodman et al. 1995. Effects of electromagnetic fields on molecules and cells. *International Review of Cytology.* Eds. Kwang et al. Academic Press vol. 158, pp. 279-339.

Goodman et al. 1998. Magnetic field stress induces expression of hsp70. *Cell Stress & Chaperones.* 3(2):79-88.

Grospietsch et al. 1995. Stimulating effects of modulated 150 MHz electromagnetic fields on the growth of *Escherichia coli* in a cavity resonator. *Bioelectrochemistry and bioenergetics.* 37:17-23.

Grundler et al. Mechanisms of electromagnetic interaction with cellular systems. *Naturwissenschafter* 79:551-559.

Grundler et al. 1982. Resonant-like dependence of yeast growth rate on microwave frequencies. *Br J Cancer Suppl.* 45(5):206-208.

Grundler W. 1978. Nonthermal effects of millimeter microwaves on yeast growth. *Z. Naturforsch.* 33c:15-22.

Grundler W. 1989. Resonant microwave effect on locally fixed yeast microcolonies. *Z. Naturforsch.* 44c:863-866.

Kim et al. 2001. Anti-stress and anti-fatigue effects of fermented rice bran. *Biosci Biotechnol Biochem.* 65(10):2294-2296.

Lin H. et al. 1994. Specific region of the c-myc promoter is responsive to electric and magnetic fields. *J Cell Biochem.* 54(3):281-288.

Lin H. et al. 1999. A magnetic field-responsive domain in the human HSP70 promoter. *J Cell Biochem.* 75:170-176.

Machado et al. 1986. Immunopharmacological effects of *Saccharomyces boulardii* in healthy human volunteers. *Int' l Immunology and Immunopathology* (United Kingdom). 8(3):245-259.

Moore RL. 1979. Biological effects of magnetic fields: studies with microorganisms. *Can. J. Microbiol.* 25:1145-1151.

Norris et al. 1997. Do bacteria sing? Sonic intercellular communication between bacteria may reflect electromagnetic intracellular communication involving coherent vibrational modes that could integrate enzyme activities and gene expression. *Mol Microbiol.* 24(4):879-80.

Ortuno et al. 2002. Oral administration of yeast, *Saccharomyces cerevisiae,* enhances the cellular innate immune response of gilthead seabream (*Sparus aurata L.* ). *Vet Immunol Immunopathol.* (Netherlands ) 85(1-2):41-50.

Phillips JL. 1993. Effects of electromagnetic field exposure on gene transcription. *J Cell Biochem.* 51(4):381-386.

Pichiko et al. 1996. Electromagnetic stimulation of productivity of microorganisms and its mechanisms. *Prikladnaya Biokhimiya I Mikrobiologiya* 32(4):468-472.

Ponne et al. 1995. Interaction of electromagnetic energy with biological material—relation to food processing. *Radiation Physics and Chemistry,* 45(4):591-607.

Romano-Spica et al. 2000. Ets1 oncogene induction by ELF-modulated 50 MHz radio frequency electromagnetic field. *Bioelectromagnetics.* 21(1):8-18.

Saha et al. 1999. Microbial Manipulation of Rumen Fermentation Using *Saccharomyces cerevisiae* as Probiotics. *Current Science* (Bangalore) 77(5):696-697.

Van Rensburg et al. 1998. Engineering yeast for efficient cellulose degradation. *Yeast.* 14(1):67-76.

Zhang et al. 1992. Electrostimulation of the dehydrogenase system of yeast by alternating currents. *Bioelectrochemistry and Bioenergetics* 28:341-353.

Zhang LY. 1994. Introduction to TLB, A Complex Microbial Fertilizer- Preliminary Application of MAB in Agriculture. *Academic Theses on TLB Complex Microbial Fertilizer.* Zhang, LY. eds. China Science and Technology Press. pp.1-17 (with English Abstract).

1983 CCCCM Catalogue of Cultures, Light Industry Publishing House, Beijing, China, 1983, pp. I-XV and 297-305.

1992 China Catalogue of Cultures, China Machine Press, Beijing, China, 1992, pp. I-XV and 164-185.

* cited by examiner

BIOLOGICAL COMPOSITIONS AND METHODS FOR TREATMENT OF COLORECTAL CANCER

This application is a divisional of U.S. application Ser. No. 10/460,341, filed Jun. 11, 2003 now U.S. Pat. No. 6,987,012, the entire disclosure of which is incorporated herein by reference in its entirety.

FIELD OF THE INVENTION

The invention relates to oral compositions comprising yeast cells that can produce a healthful benefit in a subject inflicted with colorectal cancer. The invention also relates to methods for manufacturing the oral compositions and methods of use thereof.

BACKGROUND OF THE INVENTION 2.1 Colorectal Cancer

Colorectal cancer, or cancer of the colon and rectum, is the second leading cause of cancer-related deaths in the United States, and the third most common cancer overall. The American Cancer Society estimates that each year, more than 50,000 Americans die from colorectal cancer and approximately 155,000 new cases are diagnosed, accounting for 15% of all types of tumor. Eighty to 90 million Americans (approximately 25% of the U.S. population) are considered at risk because of age or other factors. More women over the age of 75 die from colorectal cancer than from breast cancer. The 5-year survival rate remains at approximately 45%.

The exact causes of colorectal cancer are unknown, but the disease appears to be caused by both inherited and lifestyle factors. Known predisposing conditions for colorectal cancer include familial adenomatous polyposis (FAP), hereditary nonpolyposis colon cancer (HNPCC), Lynch I Syndrome, Lynch II Syndrome, inflammatory bowel disease, including both chronic ulcerative colitis (UC) and Crohn's disease, family cancer syndromes, and adenomatous polyps (sessile or tubular). In addition, a subset of patients have the propensity to develop flat polyps in the large bowel, particularly in the ascending colon. Bowel obstruction and bowel perforation are indicators of poor prognosis. Elevated pretreatment serum levels of carcinoembryonic antigen (CEA) have a negative prognostic significance. Other risk factors include high-meat, high-fat and low-fiber diets, cigarette smoking, a sedentary lifestyle, and obesity.

Colon cancer can be prevented if the polyps that lead to the cancer are detected and removed. If colon cancer is detected in its early stages, it is up to 90% curable. Fecal occult blood test (annually), sigmoidoscopy (every 5 years), double barium contrast enema (every 5 years), and colonoscopy (every 10 years) are commonly used to screen colorectal cancer. Further, a number of interesting methods such as sucrase-isomaltase now exist to qualitatively determine the degree of dysplasia and allow more precise quantification of individual patient risk for mucosal transformation in inflammatory bowel disease (Wiltz et al., 1991, *Gastroenterology* 100:1266–78).

Symptoms in patients with colorectal cancer vary depending on the site of the tumor. Circumferential adenocarcinomas of the descending colon, the sigmoid colon, and the mid to upper rectum are the most frequent causes of perturbation in bowel habits, changes in the caliber of the stool, and occasionally—in the more advanced lesions that are close to complete obstruction—paradoxical diarrhea. Other vague symptoms include constipation, blood in the stool, unexplained anemia, abdominal pain and tenderness in the lower abdomen, intestinal obstruction, weight loss with no known reason, stools narrower than usual, constant tiredness, and anal lump. In fact, most colorectal cancer patients display no definitive symptoms.

Squamous cell (epidermoid) carcinomas make up the majority of all primary colorectal cancer. The important subset of cloacogenic (basaloid transitional cell) tumors constitute the remainder. These two histologic variants are associated with human papillomavirus infection. Adenocarcinomas from anal glands or fistulae formation and melanomas are rare.

The staging of colorectal cancer is based on the revised criteria of TNM staging by the American Joint Committee for Cancer (AJCC) published in 1988. Staging is the process of describing the extent to which cancer has spread from the site of its origin. It is used to assess a patient's prognosis and to determine the choice of therapy. The stage of a cancer is determined by the size and location in the body of the primary tumor, and whether it has spread to other areas of the body. Staging involves using the letters T, N and M to assess tumors by the size of the primary tumor (T); the degree to which regional lymph nodes (N) are involved; and the absence or presence of distant metastases (M)—cancer that has spread from the original (primary) tumor to distant organs or distant lymph nodes. Each of these categories is further classified with a number 1 through 4 to give the total stage. Once the T, N and M are determined, a "stage" of I, II, III or IV is assigned. Stage I cancers are small, localized and usually curable. Stage II and III cancers typically are locally advanced and/or have spread to local lymph nodes. Stage IV cancers usually are metastatic (have spread to distant parts of the body) and generally are considered inoperable.

The primary therapy for colorectal cancer remains surgical. Usually, the entire cancer or precancerous lesion is removed and possibly some of the surrounding tissue. More extensive lymphatic or colonic resection, "no touch" techniques, and various regional radiation therapy techniques have largely been touted using anecdotal information or informally designed studies. For patients with mid and distal rectal adenocarcinomas, sphincter preservation approaches have been performed, as well as low anterior approaches with colo-anal reanastomoses. Colonic J pouches and additional physiologic modifications are also options for patients with T1, T2, and perhaps even T3 adenocarcinomas.

For Stages II and III, chemotherapy and/or radiation therapy may be added to help kill the cancer and shrink the tumor. Chemotherapy and radiation may also be used in Stage IV to improve symptoms and prolong life. However, the use of radiation therapy as a single modality in the definitive treatment of colorectal cancer has met with little success despite efforts to increase the total dose to the tumor and reduce the amount of irradiated normal tissue. Radiation therapy is rarely helpful in patients with colorectal cancer that is unsuitable for resection, as the usual reason for nonresectability is the lack of anatomic localization of the cancer. Radiation therapy is sometimes used to relieve localized obstruction, particularly in the region of the cardia, and for patients with chronically bleeding cancers that cannot be resected. The median survival for patients treated with radiation is around 12 months, and long-term survivors are few (Beatty et al., 1979, *Cancer* 43:2254–67; Newaishy et al., 1982, *Clin Radiol.* 33:347–352; Schuchman et al., 1980, *J Thorac Cardiovasc Surg.* 79:67–73).

Many chemotherapeutic drugs have been tried in the past as single agents for the palliation of colorectal cancer, but the results were generally disappointing. Nevertheless, the role of chemotherapy in the management of colorectal cancer is continually evolving. Oftentimes, chemotherapy with radiation in adjunct to surgery is used. In general, chemotherapy can achieve long-term survival rates of up to 15% to 20%, even in patients with recurrent or metastatic disease (Ali et al., 2000, *Oncology* 14(8):1223–30). Unfortunately, the high initial response rates to first line chemotherapy does not appear to translate into a survival benefit (Kohno and Kitahara, 2001, *Gan To Kagaku Ryoho* 28(4): 448–53). Moreover, there are many undesirable side effects associated with chemotherapy such as temporary hair loss, mouth sores, anemia (decreased numbers of red blood cells that may cause fatigue, dizziness, and shortness of breath), leukopenia (decreased numbers of white blood cells that may lower resistance to infection), thrombocytopenia (decreased numbers of platelets that may lead to easy bleeding or bruising), and gastrointestinal symptoms like nausea, vomiting, and diarrhea. Active chemotherapeutic agents include 5-fluorouracil, IMC-C225 (cetuximab), leucovorin, irinotecan, oxaliplatin, Camptosar (Pharmacia & Upjohn), and Celebrex.

The identification of active chemotherapeutic agents against cancers traditionally involved the use of various animal models of cancer. The mouse has been one of the most informative and productive experimental system for studying carcinogenesis (Sills et al., 2001, *Toxicol Letters* 120:187–198), cancer therapy (Malkion, 2001, *Lung Cancer* 32(3):265–279; Hoffman R M., 1999, *Invest New Drugs* 17(4):343–359), and cancer chemoprevention (Yun, 1999, *Annals NY Acad. Sci.* 889:157–192). Cancer research started with transplanted tumors in animals which provided reproducible and controllable materials for investigation. Pieces of primary animal tumors, cell suspensions made from these tumors, and immortal cell lines established from these tumor cells propagate when transplanted to animals of the same species.

To transplant human cancer to an animal and to prevent its destruction by rejection, the immune system of the animal are compromised. While originally accomplished by irradiation, thymectomy, and application of steroids to eliminate acquired immunity, nude mice that are athymic congenitally have been used as recipients of a variety of human tumors (Rygaard, 1983, in 13th International Cancer Congress Part C, Biology of Cancer (2), pp37–44, Alan R. Liss, Inc., NY; Fergusson and Smith, 1987, *Thorax*, 42:753–758). While the athymic nude mouse model provides useful models to study a large number of human tumors in vivo, it does not develop spontaneous metastases and are not suitable for all types of tumors. Next, the severe combined immunodeficient (SCID) mice is developed in which the acquired immune system is completely disabled by a genetic mutation. Human lung cancer was first used to demonstrate the successful engraftment of a human cancer in the SCID mouse model (Reddy S., 1987, *Cancer Res.* 47(9):2456–2460). Subsequently, the SCID mouse model have been shown to allow disseminated metastatic growths for a number of human tumors, particularly hematologic disorders and malignant melanoma (Mueller and Reisfeld, 1991, *Cancer Metastasis Rev.* 10(3): 193–200; Bankert et al., 2001, *Trends Immunol.* 22:386–393). With the recent advent of transgenic technology, the mouse genome has become the primary mammalian genetic model for the study of cancer (Resor et al., 2001, *Human Molec Genet.* 10:669–675).

While surgery, chemotherapeutic agents, hormone therapy, and radiation are useful in the treatment of colorectal cancer, there is a continued need to find better treatment modalities and approaches to manage the disease that are more effective and less toxic, especially when clinical oncologists are giving increased attention to the quality of life of cancer patients. The present invention provides an alternative approach to cancer therapy and management of the disease by using an oral composition comprising yeasts.

2.2 Yeast-Based Compositions

Yeasts and components thereof have been developed to be used as dietary supplement or pharmaceuticals. However, none of the prior methods uses yeast cells which have been cultured in an electromagnetic field to produce a product that has an anti-cancer effect. The following are some examples of prior uses of yeast cells and components thereof:

U.S. Pat. No. 6,197,295 discloses a selenium-enriched dried yeast product which can be used as dietary supplement. The yeast strain *Saccharomyces boulardii* sequela PY 31 (ATCC 74366) is cultured in the presence of selenium salts and contains 300 to about 6,000 ppm intracellular selenium. Methods for reducing tumor cell growth by administration of the selenium yeast product in combination with chemotherapeutic agents is also disclosed.

U.S. Pat. No. 6,143,731 discloses a dietary additive containing whole β-glucans derived from yeast, which when administered to animals and humans, provide a source of fiber in the diet, a fecal bulking agent, a source of short chain fatty acids, reduce cholesterol and LDL, and raises HDL levels.

U.S. Pat. No. 5,504,079 discloses a method of stimulating an immune response in a subject utilizing modified yeast glucans which have enhanced immunobiologic activity. The modified glucans are prepared from the cell wall of *Saccharomyces* yeasts, and can be administered in a variety of routes including, for example, the oral, intravenous, subcutaneous, topical, and intranasal route.

U.S. Pat. No. 4,348,483 discloses a process for preparing a chromium yeast product which has a high intracellular chromium content. The process comprises allowing the yeast cells to absorb chromium under a controlled acidic pH and, thereafter inducing the yeast cells to grow by adding nutrients. The yeast cells are dried and used as a dietary supplement.

Citation of documents herein is not intended as an admission that any of the documents cited herein is pertinent prior art, or an admission that the cited documents are considered material to the patentability of the claims of the present application. All statements as to the date or representations as to the contents of these documents are based on the information available to the applicant and does not constitute any admission as to the correctness of the dates or contents of these documents.

SUMMARY OF THE INVENTION

The present invention relates to biological or oral compositions useful for subjects with colorectal cancer. In one embodiment, the present invention provides biological compositions comprising live yeast cells which are capable of producing a healthful benefit in subjects with colorectal cancer. In other embodiments, the invention provides methods of making the biological compositions, and methods of using the biological compositions.

In particular, the methods of the invention comprise culturing yeast cells in the presence of a series of electromagnetic fields such that the yeast cells becomes metabolically active. The electromagnetic fields used are each defined by one of five frequency ranges and a broad range of field strength. The starting yeast cells are commercially available and/or accessible to the public, such as but not limited to *Saccharomyces*. The methods for making the biological compositions of the invention further comprise conditioning the activated yeast cells in plant extracts and the gastric juice of animals, while in the presence of another series of electromagnetic fields.

The methods of manufacturing also comprise expanding the number of activated or activated and conditioned yeast cells in large scale cultures in the presence of yet another series of electromagnetic fields, performing quality control measures, and packaging. Pharmaceutical compositions of the invention comprises activated and conditioned yeast cells and one or more pharmaceutically acceptable excipients or carriers. Additional ingredients, such as vitamins and/or flavors may be added to the biological compositions to form the oral compositions of the invention. Such additional carriers and ingredients can improve the healthful benefits, pharmacological properties, and organoleptic characteristics of the oral compositions. During the manufacturing process, the activated or activated and conditioned yeast cells may be dried and stored for a period of time.

The biological or oral compositions of the invention are ingested by the subject or used as an additive to be incorporated into food to be consumed by the subject. Dietary supplement and nutritional compositions comprising activated and conditioned yeast cells are encompassed by the invention. Preferably, the subject is a human being.

In various embodiments, the biological or oral compositions of the invention are used to produce a healthful benefit in a subject with colorectal cancer or at high risk of developing colorectal cancer. In particular, the biological composition of the invention can retard the growth of colorectal cancer cells in an animal which received the composition orally. The composition can also be used to prolong the time of survival of an animal with colorectal cancer.

DETAILED DESCRIPTION OF THE INVENTION

Figure 1:
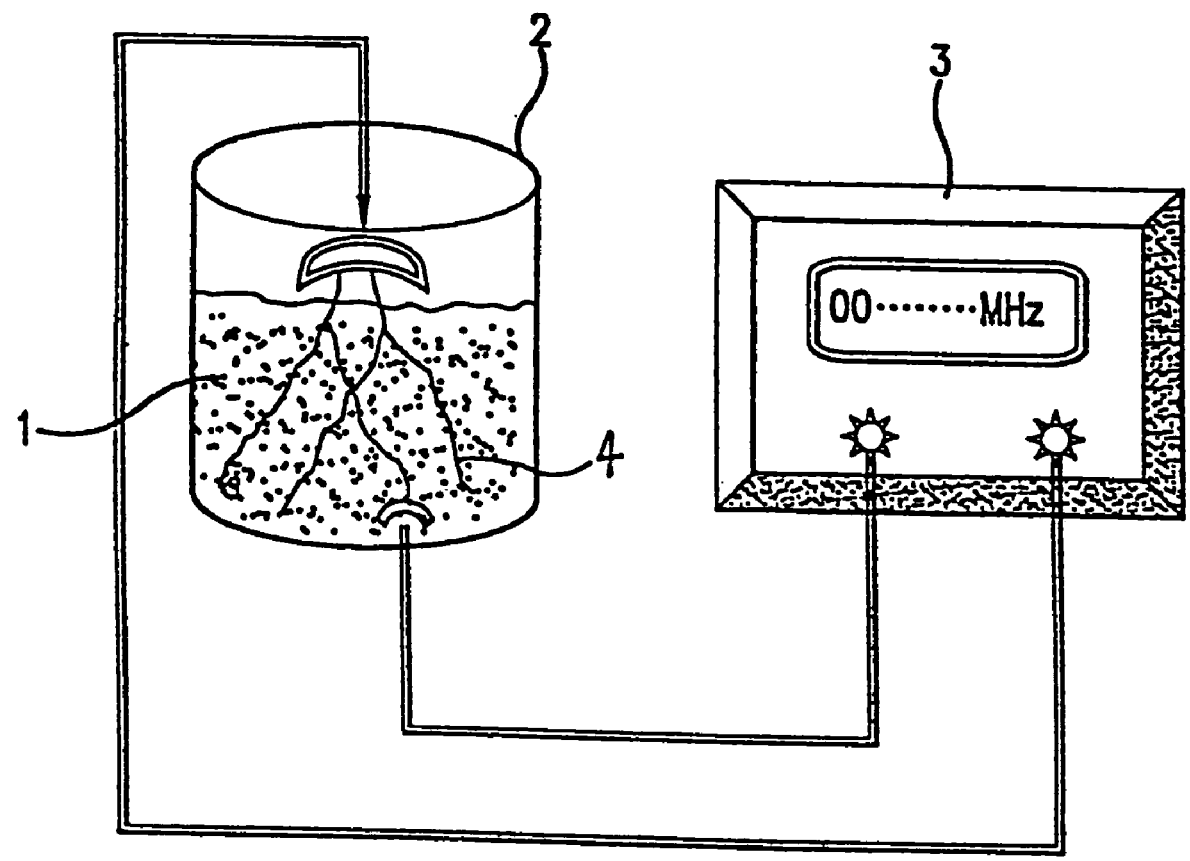
FIG. 1 Activation and conditioning of yeast cells. 1 yeast cell culture; 2 container; 3 electromagnetic field source; 4 electrode.

The present invention relates to biological compositions that can produce a healthful benefit in a subject with colorectal cancer. The present invention provides methods for manufacturing the biological compositions as well as methods for using the biological compositions.

In one embodiment, the invention provides biological compositions that comprise yeasts. Unlike the traditional use of yeasts in the making of food, the yeast cells of the invention are not used as a source of enzymes that acts on the food ingredients. The yeasts are not a primary source of nutrients for the subject. Nor are yeast cells used as a carrier, such as metal salts. The yeast cells of the invention are live when administered orally or ingested along with food by a subject. Without being bound by any theory or mechanism, the inventor believes that the culture conditions activate and/or amplified the expression of a gene or a set of genes in the yeast cells such that the yeast cells becomes highly effective in stimulating the animal's immune system, including both specific and non-specific immunological reactions, the results of which are manifested as the overall healthful benefits observed in the treated subject. The healthful benefits provided by using the biological compositions are demonstrated in animal models of human colorectal cancer which show inhibition of tumor growth and prolonged survival time of animals with the disease.

In another embodiment, the invention provides methods for making the yeast cells in the biological compositions. The starting materials are normal yeast cells which can be readily obtained commercially or from public microorganism deposits. The methods of the invention comprise a set of culture conditions that can be applied reproducibly to activate the yeast cells. The key feature of the culture conditions used in the methods of the invention is a series of alternating electromagnetic fields of defined frequency ranges and field strengths which are applied to the growing yeast cell culture. The method further comprises the step of conditioning the activated live yeast cells to the acidic environment of the stomach of the subject. The electromagnetic fields used in these methods can be created reproducibly at various scales, thus enabling even the large scale manufacturing of the biological compositions of the invention. By careful control of the culturing conditions, normal yeast cells can be activated routinely and reproducibly to become yeast cells of the invention.

In yet another embodiment, the invention provides methods for manufacturing an oral composition comprising activated and conditioned yeasts of the invention, and additional ingredients, including but not limited to pharmaceutically acceptable carriers or excipients, vitamins, herbs (including traditional Chinese medicine products), herbal extracts, minerals, amino acids, flavoring agents, coloring agents, and/or preservatives.

In yet another embodiment, the biological compositions can be added to food which will be consumed by the subject. As known to those skilled in the relevant art, many methods may be used to mix the biological or oral compositions of the invention with food while the yeast cells remain viable. In a particular embodiment, the culture broth comprising live yeast cells of the present invention are added directly to food just prior to consumption. Dried powders of the yeasts can also be reconstituted and added directly to food just prior to consumption.

In various embodiments, the oral compositions of the invention can be consumed directly by a subject or be fed directly to a subject. For example, the subject may drink the culture broth or a fraction thereof that comprises live activated and conditioned yeast cells. Oral compositions comprising dried yeast cells can also be given as a solid dosage form to the subject.

Although it is not necessary, the biological or oral compositions of the invention can be used in conjunction or in rotation with other types of treatment modalities, such as but not limited to surgery, chemotherapeutic agents, and radiation. Since the biological compositions of the invention are administered orally, the assistance of health professionals in administration of the composition is generally not essential.

Described below in Section 5.1 are the yeast cells of the invention and methods of their preparation. Section 5.2 describes the use of the biological compositions of the invention in a subject suffering from colorectal cancer. The examples in Sections 6 to 9 demonstrate the therapeutic benefits of an oral composition of the invention. The activated and conditioned yeast cells in the oral composition are characterized by their ability to (i) suppress the growth of cancer cells in an animal model of human colorectal cancer, or (ii) prolong the survival of animals with transplanted cancer cells in a model of human colorectal cancer, as compared to yeast cells which have not been activated and conditioned.

5.1 Preparation of the Yeast Cell Cultures

The yeast cells of the biological composition are produced by culturing a plurality of yeast cells in an appropriate culture medium in the presence of an alternating electromagnetic field over a period of time. The method comprises a first step of activating the yeast cells and a second step of conditioning the activated yeast cells. The activation process comprises culturing yeast cells in the presence of at least two, three, four or five electromagnetic fields of specific frequencies and field strength. The conditioning process comprises further culturing of the activated yeast cells in a medium comprising plant extracts and extracts from the stomach of an animal, in the presence of at least one electromagnetic field. The activated and conditioned yeast cells can be stored as dried cells after drying the cells under appropriate conditions. The dried activated and conditioned yeast cells can be used later in large scale culturing processes for manufacturing the biological compositions of the invention. The various culturing processes of the invention can be performed either as a batch process or a continuous process.

5.1.1 Yeasts

In various embodiments, yeasts of the genera of *Saccharomyces, Candida, Crebrothecium, Geotrichum, Hansenula, Kloeckera, Lipomyces, Pichia, Rhodosporidium, Rhodotorula, Torulopsis, Trichosporon,* and *Wickerhamia* can be used in the invention. Generally, fungi used for food manufacturing are preferred.

Non-limiting examples of yeast strains include *Saccharomyces* sp., AS2.311; *Schizosaccharomyces pombe* Linder, AS2.214, AS2.248, AS2.249, AS2.255, AS2.257, AS2.259, AS2.260, AS2.274, AS2.994, AS2.1043, AS2.1149, AS2.1178, IFFI 1056; *Saccharomyces* sake Yabe, ACCC2045; *Saccharomyces uvarum Beijer,* IFFI 1023, IFFI 1032, IFFI 1036, IFFI 1044, IFFI 1072, IFFI 1205, IFFI 1207; *Saccharomyces rouxii* Boutroux, AS2.178, AS2.180, AS2.370, AS2.371; *Saccharomyces cerevisiae* Hansen Var. ellipsoideus, ACCC2043, AS2.2, AS2.3, AS2.8, AS2.53, AS2.163, AS2.168, AS2.483, AS2.541, AS2.559, AS2.606, AS2.607, AS2.611, AS2.612; *Saccharomyces carlsbergensis* Hansen, AS2.116, AS2.162, AS2.189, AS2.200, AS2.216, AS2.265, AS2.377, AS2.417, AS2.420, AS2.440, AS2.441, AS2.443, AS2.444, AS2.459, AS2.595, AS2.605, AS2.638, AS2.742, AS2.745, AS2.748, AS2.1042; *Rhodotorula aurantiaca* (Saito)Ladder; AS2.102, AS2.107, AS2.278, AS2.499, AS2.694, AS2.703, AS2.704 and AS2.1146; *Saccharomyces cerevisiae* Hansen, ACCC2034, ACCC2035, ACCC2036, ACCC2037, ACCC2038, ACCC2039, ACCC2040, ACCC2041, ACCC2042, AS2.1, AS2.4, AS2.11, AS2.14, AS2.16, AS2.56, AS2.69, AS2.70, AS2.93, AS2.98, AS2.101, AS2.109, AS2.110, AS2.112, AS2.139, AS2.173, AS2.182, AS2.196, AS2.242, AS2.336, AS2.346, AS2.369, AS2.374, AS2.375, AS2.379, AS2.380, AS2.382, AS2.393, AS2.395, AS2.396, AS2.397, AS2.398, AS2.399, AS2.400, AS2.406, AS2.408, AS2.409, AS2.413, AS2.414, AS2.415, AS2.416, AS2.422, AS2.423, AS2.430, AS2.431, AS2.432, AS2.451, AS2.452, AS2.453, AS2.458, AS2.460, AS2.463, AS2.467, AS2.486, AS2.501, AS2.502, AS2.503, AS2.504, AS2.516, AS2.535, AS2.536, AS2.558, AS2.560, AS2.561, AS2.562, AS2.576, AS2.593, AS2.594, AS2.614, AS2.620, AS2.628, AS2.631, AS2.666, AS2.982, AS2.1190, AS2.1364, AS2.1396, IFFI 1001, IFFI 1002, IFFI 1005, IFFI 1006, IFFI 1008, IFFI 1009, IFFI 1010, IFFI 1012, IFFI 1021, IFFI 1027, IFFI 1037, IFFI 1042, IFFI 1045, IFFI 1048, IFFI 1049, IFFI 1050, IFFI 1052, IFFI 1059, IFFI 1060, IFFI 1062, IFFI 1202, IFFI 1203, IFFI 1209, IFFI 1210, IFFI 1211, IFFI 1212, IFFI 1213, IFFI 1215, IFFI 1221, IFFI 1224, IFFI 1247, IFFI 1248, IFFI 1251, IFFI 1270, IFFI 1277, IFFI 1289, IFFI 1290, IFFI 1291, IFFI 1292, IFFI 1293, IFFI 1297, IFFI 1300, IFFI 1301, IFFI 1302, IFFI 1307, IFFI 1308, IFFI 1309, IFFI 1310, IFFI 1311, IFFI 1331, IFFI 1335, IFFI 1336, IFFI 1337, IFFI 1338, IFFI 1339, IFFI 1340, IFFI 1345, IFFI 1348, IFFI 1396, IFFI 1397, IFFI 1399, IFFI 1441 and IFFI 1443. Preferred yeast strains include but are not limited to *S. cerevisiae* AS2.501, AS2.502, AS2.503, AS2.504, AS2.535, AS2.558, AS2.560, AS2.561 and AS2.562.

Generally, yeast strains useful for the invention can be obtained from private or public laboratory cultures, or publicaly accessible culture deposits, such as the American Type Culture Collection, 10801 University Boulevard, Manassas, Va. 20110-2209 and the China General Microbiological Culture Collection Center (CGMCC), China Committee for Culture Collection of Microorganisms, Institute of Microbiology, Chinese Academy of Sciences, Haidian, P.O. Box 2714, Beijing, 100080, China.

Non-limiting examples of using yeast cells of the invention with *Saccharomyces cerevisiae* Hansen strain AS2.1396 are provided in Sections 6 to 9 herein below. The yeast cells of the invention do not comprise an enhanced level of selenium or chromium relative to that found in naturally occurring yeast cells. In certain embodiments, the biological compositions do not comprise cells of *Saccharomyces boulardii* (for example, ATCC Accession No. 74366) or cells of a particular strain of *Saccharomyces cerevisiae* (strain Hansen CBS 5926) that is also commonly referred to as *Saccharomyces boulardii*.

Although it is preferred, the preparation of the yeast cells of the invention is not limited to starting with a pure strain of yeast. The yeast cells in the biological compositions may be produced by culturing a mixture of yeast cells of different species or strains. The constituents of a mixture of yeast cells can be determined by standard yeast identification techniques well known in the art.

In various embodiments of the invention, standard techniques for handling, transferring and storing yeasts are used. Although it is not necessary, sterile conditions or clean environments are highly desirable when carrying out the manufacturing processes of the invention, especially when the biological compositions are for human consumption. The manufacturing process can be adapted to meet regulatory guidelines on product safety and quality control by standard practice known in the art.

5.1.2 Electromagnetic Fields

As used herein, the terms "alternating electromagnetic field", "electromagnetic field" or "EM field" are synonymous. An electromagnetic field useful in the invention can be generated by various means well known in the art. A schematic illustration of exemplary setups are depicted respectively in FIG. 1. An electromagnetic field of a desired frequency and a desired field strength is generated by an electromagnetic wave source (3) which comprises one or more signal generators that are capable of generating electromagnetic waves, preferably sinusoidal waves, and preferably in the frequency range of 1,500 to 15,000 MHz and most preferably 7,900 to 12,800 MHz. Such signal generators are well known in the art. Signal generators capable of generating signal with a narrower frequency range can also be used. If desirable, a signal amplifier can also be used to increase the output signal, and thus the strength of the EM field.

The electromagnetic field can be applied to the culture by a variety of means including placing the yeast cells in close proximity to a signal emitter connected to a source of electromagnetic waves. The signal generator is connected to the signal emitter by cables such as coaxial cables that can transmit signals up to greater than or equal to 30 GHz. Typically, the yeast cells are placed in a container which is made of material that is not an electric conductor, such as but not limited to plastic, resin, glass, and ceramic.

In one embodiment, the electromagnetic field is applied by signal emitters in the form of electrodes (4) that are submerged in a culture of yeast cells (1). In a preferred embodiment, one of the electrodes is a metal plate which is placed on the bottom of a non-conducting container (2), and the other electrode comprises a plurality of wires or tubes so configured inside the container such that the energy of the electromagnetic field can be evenly distributed in the culture. The electrodes are preferably made of copper. For an upright culture vessel, the tips of the wires or tubes are placed within 3 to 30 cm from the bottom of the vessel (i.e., approximately 2% to 10% of the height of the vessel from the bottom). Table 1 provides exemplary set up for culturing the yeast cells of the invention.

TABLE 1

| height of culture medium in the non-conducting container (cm) | distance electrodes are placed from the bottom of the container (cm) | range for distance of the electrodes from the bottom (cm) |
| --- | --- | --- |
| 15 to 20 | 3 | 3 to 5 |
| 20 to 30 | 5 | 5 to 7 |
| 30 to 50 | 7 | 7 to 10 |
| 50 to 70 | 10 | 10 to 15 |
| 70 to 100 | 15 | 15 to 20 |
| 100 to 150 | 20 | 20 to 30 |
| 150 to 200 | 30 | 25 to 30 |

The number of electrodes used depends on both the volume of the culture and the diameter of the electrode. For example, for a culture having a volume of 10 liter or less, two or three electrodes having a diameter of between 0.5 to 2.0 mm can be used. For a culture volume of 10 to 100 liter of culture, the electrodes can have a diameter of 3.0 to 5.0 mm. For a culture volume of 100 to 1,000 liter, the electrodes can have a diameter of 6.0 to 15.0 mm. For a culture having a volume greater than 1,000 liter, the electrodes can have a diameter of between 20.0 to 25.0 mm.

5.1.3 Activation of Yeast Cells

According to the invention, the method for producing activated yeast cells of the invention comprises culturing yeast cells in the presence of at least two, three, four or five alternating electromagnetic (EM) fields.

The culture process can be initiated by inoculating 1,000 ml of medium with an inoculum of a selected yeast strain (such as one of those described in Section 5.1.1) such that the starting cell density of the culture is greater than about $10^5$ cells per ml. For example, *Saccharomyces cerevisiae* Hansen strain AS2.1396 can be used. The starting culture can be used to seed larger scale culture. The culture is maintained initially at 28° C. to 32° C. for 22 to 30 hours prior to exposure to the EM field(s), typically at 30° C. for 28 hours.

The culturing process may preferably be conducted under conditions in which the concentration of dissolved oxygen is between 0.025 to 0.08 mol/m$^3$, preferably 0.04 mol/m$^3$. The oxygen level can be controlled by any conventional means known in the art, including but not limited to stirring and/or bubbling.

The culture is most preferably carried out in a liquid medium which contains sources of nutrients assimilable by the yeast cells. Table 2 provides an exemplary medium for culturing the yeast cells of the invention.

TABLE 2

| Medium Composition | Quantity |
| --- | --- |
| Sucrose or glucose | 20 g |
| Vitamin $B_6$ | 50 µg |
| Vitamin $B_{12}$ | 50 µg |
| Fetal calf serum | 30 ml |
| Vitamin A | 60 µg |
| $KH_2PO_4$ | 0.20 g |
| $MgSO_4 \cdot 7H_2O$ | 0.25 g |
| NaCl | 0.30 g |
| $CaSO_4 \cdot 2H_2O$ | 0.20 g |
| $CaCO_3 \cdot 5H_2O$ | 4.0 g |
| Peptone | 2.5 g |
| Autoclaved water | 1,000 ml |

The culturing medium is heated to 45° C. and cooled before adding the vitamin $B_6$, vitamin $B_{12}$, fetal calf serum, and vitamin A.

In general, carbohydrates such as sugars, for example, sucrose, glucose, fructose, dextrose, maltose, xylose, and the like and starches, can be used either alone or in combination as sources of assimilable carbon in the culture medium. The exact quantity of the carbohydrate source or sources utilized in the medium depends in part upon the other ingredients of the medium but, in general, the amount of carbohydrate usually varies between about 0.1% and 5% by weight of the medium and is preferably between about 0.2% and 2%. These carbon sources can be used individually, or several such carbon sources may be combined in the medium. Among the inorganic salts which can be incorporated in the culture media are the customary salts capable of yielding sodium, calcium, phosphate, sulfate, carbonate, and like ions. Non-limiting examples of nutrient inorganic salts are $KH_2PO_4$, $(NH_4)_2HPO_4$, $CaCO_3$, $MgSO_4$, NaCl, and $CaSO_4$.

It should be noted that the composition of the media provided in Table 2 is not intended to be limiting. The process can be scaled up or down according to needs. Various modifications of the culture medium may be made by those skilled in the art, in view of practical and economic considerations, such as the scale of culture and local supply of media components.

In certain embodiments, a series of at least two, three, four or five EM fields are applied to the culture of yeast cells, each having a different frequency within a stated range, and a different field strength within a stated range. The EM fields can be applied in any order and by any means known in the art, such as the apparatus described in Section 5.1.2. Although any of the following two, three or four EM fields can be applied, preferably, all five EM fields are applied.

For the first EM field, the frequency is in the range of 7,941 to 7,950 MHz and the field strength is in the range of 230 to 250 mV/cm. The yeast culture is exposed to this first EM field at 30±2° C. for about 24 hours.

For the second EM field, the frequency is in the range of 9,131 to 9,140 MHz and the field strength is in the range of 220 to 240 mV/cm. The yeast culture is exposed to this second EM field at 30±2° C. for about 10 hours.

For the third EM field, the frequency is in the range of 9,991 to 10,000 MHz and the field strength is in the range of 250 to 270 mV/cm. The yeast culture is exposed to this third EM field at 30±2° C. for about 22 hours.

For the fourth EM field, the frequency is in the range of 11,141 to 11,150 MHz and the field strength is in the range of 230 to 250 mV/cm. The yeast culture is exposed to this fourth EM field at 30±2° C. for about 10 hours.

For the fifth EM field, the frequency is in the range of 12,771 to 12,780 MHz and the field strength is in the range of 260 to 280 mV/cm. The yeast culture is exposed to this fifth EM field at 30±2° C. for about 22 hours.

In less preferred embodiments, the yeast cells can be cultured by exposure to two, three or four of the above-mentioned EM fields in a different order. The yeast cells can remain in the same container and use the same set of electromagnetic wave generator and emitters when switching from one EM field to another EM field.

The cell density of the culture at the end of the activation process is typically greater than about $10^6$ to $10^9$ cells per ml (estimated by hematocytometer). The activated yeast cells may be recovered from the culture by various methods known in the art, and stored at a temperature below about 0° C. to 4° C. The activated yeast cells recovered from the liquid culture may be dried and stored in powder form. Preferably, the powder form of the yeast cells comprises greater than about $10^7$ to $10^{10}$ yeast cells per gram.

5.1.4 Conditioning of Yeast Cells

According to the invention, performance of the activated yeast cells can be optimized by culturing the activated yeast cells in the presence of an extract from the stomach (e.g., the gastric juice) of an animal with physiology similar to the subject to which the biological composition will be administered. The inclusion of this additional conditioning process allows the activated yeast cells to adapt to and endure the acidic environment of the subject's stomach. The method for conditioning activated yeast cells of the invention comprises culturing yeast cells in such materials in the presence of at least one EM field.

The culture process can be initiated by inoculating 1,000 ml of a conditioning medium with about 10 gram of dried activated yeasts containing about $10^{10}$ cells per gram (as prepared by the methods described in Section 5.1.3). An equivalent number of yeast cells in culture, preferably greater than $10^6$ to $10^9$ cells per ml, more preferably at $10^8$ cells per ml, can also be used as an inoculum. The conditioning medium comprises per 1,000 ml about 700 ml of gastric juice of an animal and about 300 ml of wild hawthorn juice. The process can be scaled up or down according to needs.

The gastric juice of an animal can be obtained from the stomach content of a freshly slaughtered animal. Although not essential, the animal is preferably kept under a clean environment, and fed a standard diet, preferably germ-free. For example, the content of the stomach of a 120-day old pig is mixed with 2,000 ml of distilled water, and allowed to settle without stirring for 6 hours. The clear liquid above is collected for use as the gastric juice used in the conditioning process. The gastric juice of a pig can be used to condition yeast cells for use in a variety of mammals, including humans. Other methods that can be used to collect the gastric juice include centrifugation or filtration of the mixture to remove debris and/or microorganisms. The gastric juice so obtained can be stored at 4° C. Preferably, the collection procedures and storage are carried out under sterile conditions.

The wild hawthorn juice is an extract of wild hawthorn fruits prepared by slicing the fruits and drying the slices in air, preferably to less than 8% moisture (commercial dryer can be used if necessary), crushing the dried fruits to less than 20 mesh, and mixing 1,500 ml of water per 500 gram of the crushed wild hawthorn. The mixture is then allowed to settle without stirring for 6 hours, and the clear liquid above is collected for use as the wild hawthorn juice used in the conditioning process. Other methods that can be used to collect the hawthorn juice include centrifugation or filtration of the mixture. Preferably, the collection procedures and storage are carried out under sterile conditions.

The activated yeast cells are conditioned by culturing in at least one of the following two EM fields which can be applied by the apparatus described in Section 5.1.2 or any means known in the art:

The first EM field has a frequency in the range of 11,141 to 11,150 MHz and a field strength in the range of 230 to 250 mV/cm. The temperature is maintained at 28° C. to 32° C., and typically at 30° C. The yeast culture is exposed to this first EM field for about 12 hours.

The second EM field has a frequency in the range of 12,771 to 12,780 MHz and a field strength in the range of 290 to 310 mV/cm. The temperature is maintained at 28° C. to 32° C., and typically at 30° C. The yeast culture is exposed to this second EM field for about 36 hours.

In a preferred embodiment, the activated yeast cells are conditioned by culturing in both of the above-mentioned EM fields. In less preferred embodiments, the yeast cells are conditioned in the two different EM fields in a different order. In other embodiments, a series of EM fields having field characteristics within the ranges stated above can be applied to condition the yeast cells. The yeast cells can remain in the same container and use the same set of electromagnetic wave generator and emitters when switching from one EM field to another EM field.

The cell density of the culture at the end of the activation process is typically greater than about $10^7$ to $10^{10}$ cells per ml (estimated by hematocytometer). The activated and conditioned yeast cells may be recovered from the culture by various methods known in the art, and stored at a temperature below about 0° C. to 4° C.

The activated and conditioned yeast cells can be used directly in a biological composition or used as a starter culture for large scale manufacturing. The activated and conditioned yeast cells recovered from the liquid culture may be dried and stored in powder form. Preferably, the powder form of the activated and conditioned yeast cells comprises greater than about $10^8$ to $10^{11}$ yeast cells per gram.

5.1.5 Large Scale Manufacturing

The present invention also encompasses methods of manufacturing of the biological compositions of the invention at a large scale. The activated and conditioned yeast cells as prepared by Sections 5.1.3 and 5.1.4 are propagated on a large scale to make the biological compositions of the invention. The method comprises culturing the yeast cells in the presence of one or more EM fields for a period of time, diluting the growing yeast cells with fresh medium, and repeating the process. The method can be carried out as a batch process or a continuous process.

Figure 2:
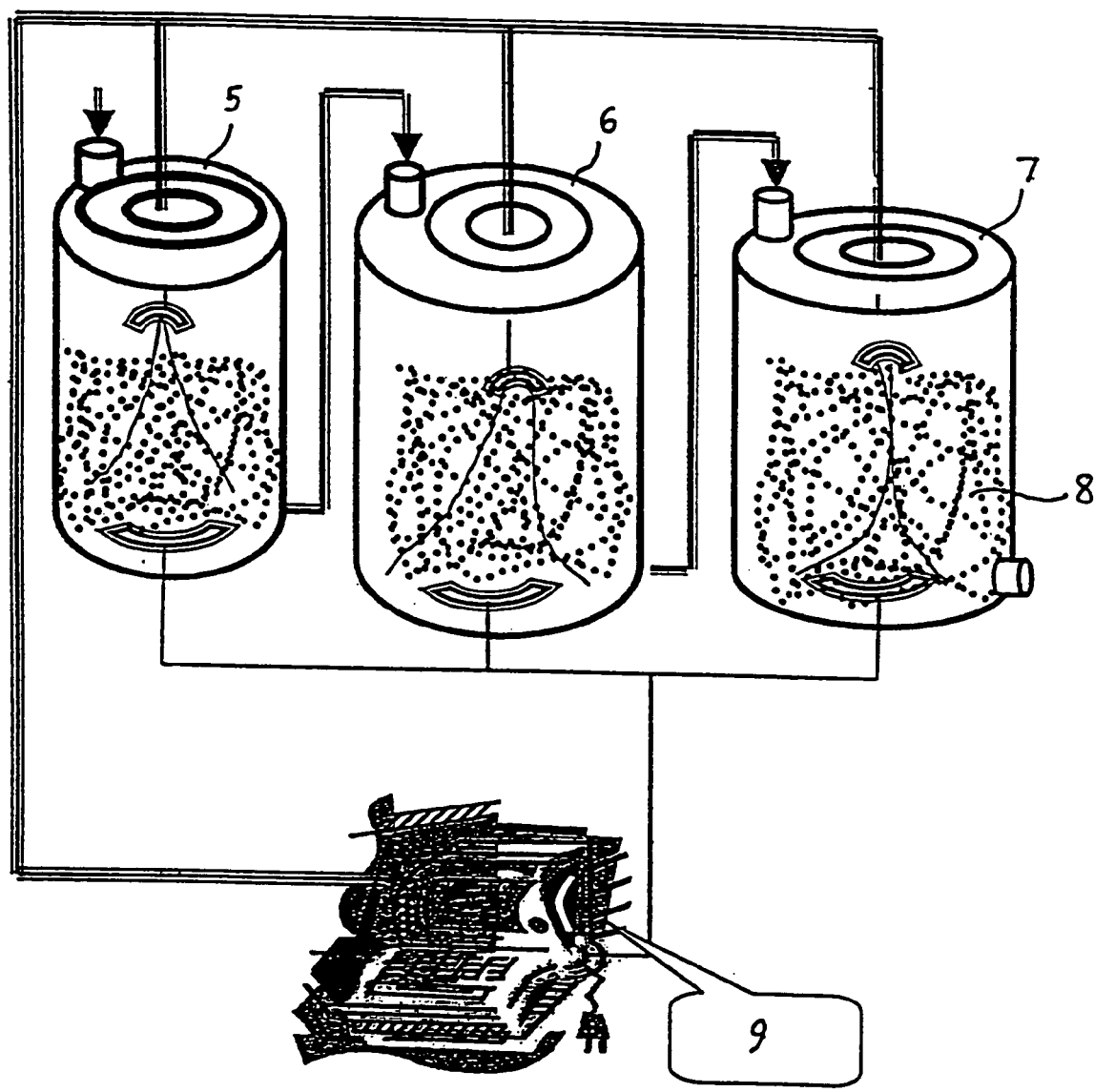
FIG. 2 Large scale propagation of yeast cells. 5 first container; 6 second container; 7 third container; 8 yeast cell cultures; 9 electromagnetic field source.

In one preferred embodiment, a set of three containers (5, 6, 7) each comprising a set of electrodes for generating an electromagnetic field as described in Section 5.1.2 are set up each with 1,000 liters of a culture medium. See FIG. 2. The culture medium comprises nutrients assimilable by the yeast cells as shown in Table 3.

TABLE 3

| Material | Quantity |
| --- | --- |
| Wild hawthorn juice | 300 liters |
| Jujube juice | 300 liters |
| Wu wei zi juice | 300 liters |
| Soybean juice | 100 liters |

The wild hawthorn juice is an extract of fresh wild hawthorn fruits prepared by washing the fruits clean, drying the fruits in air or using a commercial dryer to less than 8% moisture, crushing the dried fruits to less than 20 mesh, and mixing the crushed wild hawthorn with water at a ratio of 400 liters of water per 100 kg of crushed fruits. The mixture is then stirred continuously for 12 hours while the temperature is maintained at 28° C. to 30° C. The mixture is then centrifuged at 1,000 rpm to collect the supernatant which is used as described above. Preferably, the procedures are carried out under sterile conditions.

The jujube juice is an extract of fresh jujube fruits prepared by washing the fruits clean, drying the fruits to less than 8% moisture, crushing the dried fruits to less than 20 mesh, and mixing the crushed jujube with water at a ratio of 400 liters of water per 100 kg of crushed fruits. The mixture is then stirred continuously for 12 hours while the temperature is maintained at 28° C. to 30° C. The mixture is then centrifuged at 1,000 rpm to collect the supernatant which is used as described above. Preferably, the procedures are carried out under sterile conditions.

The wu wei zi juice is an extract of fresh berries of *Schisandra chinensis* plant prepared by washing the berries, drying the fruits to less than 8% moisture, crushing the dried berries to less than 20 mesh, and mixing the crushed berries with water at a ratio of 400 liters of water per 100 kg of crushed berries. The mixture is then stirred continuously for 12 hours while the temperature is maintained at 28° C. to 30° C. The mixture is then centrifuged at 1,000 rpm to collect the supernatant which is used as described above. Preferably, the procedures are carried out under sterile conditions.

The soybean juice is prepared by washing the soybeans, drying the soybeans to less than 8% moisture, crushing the soybeans to less than 20 mesh, and mixing the crushed soybeans with water. For 30 kg of soybeans, 130 liters of water is used. The mixture is then stirred continuously for 12 hours while the temperature is maintained at 28° C. to 30° C. The mixture is then centrifuged at 1,000 rpm to collect the supernatant which is used as described above. Preferably, the procedures are carried out under sterile conditions.

The first container is inoculated with activated or activated and conditioned yeast cells as prepared by the methods of Sections 5.1.4 and 5.1.5. About 1,000 gram of dried yeast powder are added to 1,000 liter of culture medium. Each gram of the dried yeast powder comprises about $10^{10}$ yeast cells. Instead of dried yeast cells, an equivalent number of yeast cells in a liquid medium can also be used, preferably greater than about $10^6$ to $10^9$ cells per ml, more preferably about $10^7$ cells per ml.

The yeast cells in the first container (5) are then subjected to a series of two EM fields. For the first EM field, which can be applied by the apparatus described in Section 5.1.2, the frequency is in the range of 11,141 to 11,150 MHz and the field strength is in the range of 280 to 300 mV/cm. The yeast culture is exposed to this first EM field for about 8 hours.

The yeast cells are then subjected to a second EM field having a frequency in the range of 12,771 to 12,780 MHz and a field strength in the range of 310 to 330 mV/cm. The yeast culture is exposed to this second EM field for about 10 hours. The yeast cells from the first container are then transferred to the second container which contains about 1,000 liter of the culture medium. In effect, the first yeast culture is diluted by about 50% with fresh culture medium.

In the second container (6), the yeast cells are again subjected to a series of two EM fields. The frequencies used in the second container are similar to those used in the first container but the field strengths are marginally lower. The first EM field has a frequency in the range of 11,141 to 11,150 MHz and a field strength in the range of 280 to 300 mV/cm. The yeast culture is exposed to this EM field for about 8 hours. The yeast cells are then subjected to a second EM field having a frequency in the range of 12,771 to 12,780 MHz and a field strength in the range of 330 to 350 mV/cm. The yeast culture is exposed to this second EM field for about 12 hours. The yeast cells from the second container are then transferred to the third container which contains yet another 1,000 liter of the culture medium. Again, the second yeast culture is diluted by about 50% with fresh culture medium.

In the third container (7), the yeast cells are again subjected to a series of two EM fields. The frequencies used in the third container are similar to those used in the first and second container but the field strengths are lower. The first EM field has a frequency in the range of 11,141 to 11,150 MHz and field strength in the range of 180 to 200 mV/cm. The yeast culture is exposed to this EM field for about 12 hours. The yeast cells are then subjected to a second EM field having a frequency in the range of 12,771 to 12,780 MHz and a field strength in the range of 230 to 250 mV/cm. The yeast culture is exposed to this EM field for about 24 hours.

The yeast cell culture resulting from the end of this stage can be used directly as an oral composition of the invention, or used to form other compositions encompassed by the invention.

The cell density of the culture at the end of the large scale manufacturing process is typically greater than about $10^8$ to $10^{10}$ cells per ml (estimated by hematocytometer). The concentration of yeast cells in the medium can be concentrated or diluted accordingly. In certain embodiments, the concentration of yeast cells in the medium is in the range of $10^3$ to $10^{10}$ cells per ml. In less preferred embodiments, the concentration of yeast cells in the medium is in the range of $10^3$ to $10^6$ cells per ml. In more preferred embodiments, the concentration of yeast cells in the medium is greater than $10^6$ to $10^{10}$ cells per ml. In most preferred embodiments, the concentration of yeast cells in the medium is in the range of $10^6$ to $5 \times 10^8$ cells per ml.

Other ingredients that enhance the healthful benefits, pharmacological properties and/or organoleptic characteristics of the composition can be added to the yeast cell culture. To maintain viability and freshness of the composition, it is preferred that the various downstream and packaging process be carried out below room temperature, and preferably at 0° C. to 4° C. In one embodiment, the yeast cell culture can be packaged in liquid containers.

In another embodiment, the activated and conditioned yeast cells can be dried as follows. The yeast cell culture is first centrifuged under 75 to 100 g for 10 to 20 minutes to remove the supernatant. The residue which may contain up to 85% moisture is dried in a first dryer at a temperature not exceeding 60±2° C. for a period of 5 minutes so that yeast cells quickly became dormant. The yeast cells were then sent to a second dryer and dried at a temperature not exceeding 65±2° C. for a period of about 8 minutes to further remove at least 10%, at least 20%, at least 30%, at least 40%, at least 50%, at least 60%, at least 70%, at least 80%, at least 90%, at least 95%, at least 98%, or at least 99% of water. For example, the yeast cells may be dried to remove at least 88% of water so the dried yeast cells may contain up to 12% moisture.

After cooling to room temperature, the dried yeast cells can be packaged by standard pharmaceutical methods in various solid dosage form, each containing a predetermined amount of the dried material. In a preferred embodiment, the dried material comprises about $10^5$ to $10^{11}$ cells per gram. In a more preferred embodiment, the dried material comprises about $10^8$ to $5 \times 10^{10}$ cells per gram. In a most preferred embodiment, the dried material comprises about $5 \times 10^8$ cells per gram.

In general, the compositions are prepared by uniformly and intimately admixing the active ingredient with liquid carriers or finely divided solid carriers.

5.1.6 Preferred Embodiments

In one preferred embodiment, the invention provides a method for preparing a biological composition comprising activated and conditioned yeast cells, said method comprising in any order the steps of:

(a) culturing the yeast cells in a first electromagnetic field having a frequency at 7,948 MHz and a field strength of 231 mV/cm;

(b) culturing the yeast cells in a second electromagnetic field having a frequency at 9,135 MHz and a field strength of 221 mV/cm;

(c) culturing the yeast cells in a third electromagnetic field having a frequency at 9,997 MHz and a field strength of 254 mV/cm;

(d) culturing the yeast cells in a fourth electromagnetic field having a frequency at 11,148 MHz and a field strength of 233 mV/cm; and (e) culturing the yeast cells in a fifth electromagnetic field having a frequency at 12,778 MHz and a field strength of 266 mV/cm; and after the last of the first five steps, the following steps in any order:

(f) culturing the yeast cells in a liquid medium comprising wild hawthorn juice and gastric juice of a mammal in a sixth electromagnetic field having a frequency at 11,148 MHz and a field strength of 242 mV/cm; and (g) culturing the yeast cells in a liquid medium comprising wild hawthorn juice and gastric juice of a mammal in a seventh electromagnetic field having a frequency at 12,778 MHz and a field strength of 293 mV/cm.

The activated and conditioned yeast cells obtained at the conclusion of this method is encompassed by the invention. Preferably, the yeast cells are *Saccharomyces cerevisiae* Hansen strain AS2.1396. These yeast cells can be used in the following method of further expanding number of activated and conditioned yeast cells.

In another preferred embodiment, the invention provides a method of mass producing a biological composition comprising activated and conditioned yeast cells, said method comprising culturing the activated and conditioned yeast cells prepared by the preferred embodiment described above in this section, in a medium comprising wild hawthorn juice, jujube juice, wu wei zi juice, and soybean juice, and in the presence of one or more series of electromagnetic fields. Each series of EM fields comprises two EM fields in the order stated:

(h) an eighth electromagnetic field or series of electromagnetic fields having a frequency at 11,148 MHz and a field strength in the range of 180 to 300 mV/cm, preferably at three fields strengths, e.g., in the order of 286 mV/cm, 292 mV/cm, and 188 mV/cm; and (i) a ninth electromagnetic field or series of electromagnetic fields having a frequency at 12,778 MHz and a field strength in the range of 230 to 350 mV/cm, preferably at three fields strengths, e.g., in the order of 322 mV/cm, 332 mV/cm, and 236 mV/cm.

The series may be repeated several times, such as three times, each time using a slightly lower field strength.

5.2 Methods of Uses 5.2.1 Uses in Subjects with Colorectal Cancer

The present invention further provides methods of use of the biological compositions of the invention. In one embodiment, the biological composition is used as a medicament for treatment of colorectal cancer. In another embodiment, the biological composition is used as a dietary supplement, health food, or health drink. The methods comprise administering an effective amount of the biological composition to a subject in need. The biological composition may be administered orally, in liquid or solid form, or enterally through a feeding tube. As used herein, the term "an effective amount" means an amount sufficient to provide a therapeutic or healthful benefit in the context of colorectal cancer.

According to the invention, the biological composition can produce a healthful benefit in a subject suffering from colorectal cancer. Preferably, the subject is a human being. The subject in need is one who is diagnosed with colorectal cancer, with or without metastasis, at any stage of the disease (e.g., TX, T0, Tis, T1, T2, T3, T4, NX, N0, N1, MX, M0 and M1). As used herein, the term "colorectal cancer" includes but is not limited to squamous cell (epidermoid) carcinomas, cloacogenic (basaloid transitional cell) tumors, and adenocarcinomas.

The subject may be a colorectal cancer patient who is receiving concurrently other treatment modalities against the colorectal cancer. The subject can be a colorectal cancer patient who had undergone a regimen of treatment (e.g., chemotherapy and/or radiation) and whose cancer is regressing. The subject may be a colorectal cancer patient who had undergone a regimen of treatment (e.g., surgery) and who appears to be clinically free of the colorectal cancer. The biological composition of the invention can be administered adjunctively with any of the treatment modalities, such as but not limited to chemotherapy, radiation, and/or surgery. For example, the biological composition can be used in combination with one or more chemotherapeutic or immunotherapeutic agents, such as 5-fluorouracil, IMC-C225 (cetuximab), leucovorin, irinotecan, oxaliplatin, Camptosar (Pharmacia & Upjohn), and Celebrex. The biological composition can also be used after other regimen(s) of treatment is concluded.

The subject may be one who has not yet been diagnosed with colorectal cancer but are predisposed to or at high risk of developing colorectal cancer as a result of genetic factors and/or environmental factors. The subject may also be one who displays characteristics that are associated with a high risk of colorectal cancer, such as nodules detected by computer tomographic scanning or suspect cells in biopsy and/or body fluids.

Depending on the subject, the therapeutic and healthfiil benefits range from inhibiting or retarding the growth of the colorectal cancer and/or the spread of the colorectal cancer to other parts of the body (i.e., metastasis), palliating the symptoms of the cancer, improving the probability of survival of the subject with the cancer, prolonging the life expectancy of the subject, improving the quality of life of the subject, and/or reducing the probability of relapse after a successful course of treatment (e.g., surgery, chemotherapy or radiation). The symptoms associated with colorectal cancer include constipation, blood in the stool, unexplained anemia, abdominal pain and tenderness in the lower abdomen, intestinal obstruction, weight loss with no known reason, stools narrower than usual, constant tiredness, and anal lump.

In particular, the invention provides a method for retarding the growth of colorectal cancer cells in a subject, such as a human, comprising administering orally to the subject a biological composition of the invention. The invention also provide a method for prolonging the time of survival of a subject inflicted with colorectal cancer, preferably a human patient, comprising administering orally to the subject a biological composition of the invention.

The effective dose will vary with the subject treated. The effective dose for the subject will also vary with the condition to be treated and the severity of the condition to be treated. The dose, and perhaps the dose frequency, will also vary according to the age, body weight, and response of the individual subject. In general, the total daily dose range of activated and conditioned yeast cells for a subject inflicted with colorectal cancer is from about $10^5$ to $10^{11}$ cells per day, preferably, about $10^8$ to $5 \times 10^{10}$ cells per day; more preferably, about $2 \times 10^9$ cells per day in powder form or $9 \times 10^8$ to $1 \times 10^{10}$ cells per day in liquid preparations, administered in single or divided doses orally. The length of time for a course of treatment should be at least 1 week, at least 2 weeks, at least 3 weeks, at least 4 weeks, at least 5 weeks, at least 7 weeks, at least 10 weeks, at least 13 weeks, at least 15 weeks, at least 20 weeks, at least 6 months, or at least 1 year. It may be necessary to use dosages outside these ranges in some cases as will be apparent to those skilled in the art. In certain embodiments, the oral compositions can be administered for a period of time until the symptoms and/or infection of the patients by the bacteria and viruses are under control, or when the disease has regressed partially or completely. For use as a dietary supplement, the total daily dose range should be from about $10^5$ to $10^{11}$ cells per day; preferably, about $5 \times 10^7$ to $5 \times 10^9$ cells per day. The oral compositions can be administered as a dietary supplement for as long as 6 months, or in accordance with recommended length of use under the Dietary Supplement Health and Education Act (DSHEA) or other government or industry guidelines. Further, it is noted that the nutritionist, dietician, clinician or treating physician will know how and when to interrupt, adjust, or terminate use of the biological composition as a medicament or dietary supplement in conjunction with individual patient response.

The effect of the biological compositions of the invention on development and progression of colorectal cancer can be monitored by any methods known to one skilled in the art, including but not limited to measuring: a) changes in the size and morphology of the tumor using imaging techniques such as a computed tomographic (CT) scan or a sonogram; and b) changes in levels of biological markers of risk for colorectal cancer.

5.2.2 Formulations

The biological compositions of the present invention comprise activated and conditioned live yeast cells prepared as described above in Section 5.1, as active ingredient, and can optionally contain a pharmaceutically acceptable carrier or excipient, and/or other ingredients provided that these ingredients do not kill or inhibit the yeast cells. Other ingredients that can be incorporated into the biological compositions of the present invention, may include, but are not limited to, herbs (including traditional Chinese medicine products), herbal extracts, vitamins, amino acids, metal salts, metal chelates, coloring agents, flavor enhancers, preservatives, and the like.

Any dosage form may be employed for providing the subject with an effective dosage of the oral composition. Dosage forms include tablets, capsules, dispersions, suspensions, solutions, and the like. In one embodiment, compositions of the present invention suitable for oral administration may be presented as discrete units such as capsules, cachets, or tablets, each containing a predetermined amount of activated and conditioned yeast cells, as a powder or granules or as a solution or a suspension in an aqueous liquid, a non-aqueous liquid, an oil-in-water emulsion, or a water-in-oil liquid emulsion. In general, the compositions are prepared by uniformly and intimately admixing the active ingredient with liquid carriers or finely divided solid carriers or both, and then, if necessary, shaping the product into the desired presentation. Such products can be used as pharmaceuticals or dietary supplements, depending on the dosage and circumstances of its use.

The oral compositions of the present invention may additionally include binding agents (e.g., pregelatinized maize starch, polyvinylpyrrolidone or hydroxypropyl methylcellulose); binders or fillers (e.g., lactose, pentosan, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets or capsules can be coated by methods well known in the art.

Liquid preparations for oral administration can take the form of, for example, solutions, syrups or suspensions, or they can be presented as a dry product for constitution with water or other suitable vehicle before use. The temperature of the liquid used to reconstitute the dried product should be less than 65° C. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). As described below, the preparations can also be made to resemble foods or beverages, containing buffer salts, flavoring, coloring and sweetening agents as appropriate. In certain embodiments, the oral composition is a cell suspension comprising about $10^3$ to $10^{10}$ cells per ml. The oral composition can be produced by diluting or concentrating the yeast culture medium produced by the method of Section 5.1.5 as required. In less preferred embodiments, the oral composition is a cell suspension containing about $10^3$ to $10^6$ cells per ml. In more preferred embodiments, the oral composition is a cell suspension containing greater than about $10^6$ to $10^{10}$ cells per ml. In most preferred embodiments, the oral composition is a cell suspension containing about $10^6$ to $5 \times 10^8$ cells per ml. The oral composition can be formulated as a health drink and packaged in liquid containers, each containing a predetermined amount of the liquid yeast culture. Standard methods of quality control and packaging are applied to produce in one embodiment of the invention, oral compositions packaged in liquid containers each comprising about 1 ml, 2 ml, 3 ml, 4 ml, 5 ml, 10 ml, 15 ml, 20 ml, 30 ml, 40 ml, 50 ml, 75 ml, 100 ml, 150 ml, 200 ml, 250 ml, 500 ml, 750 ml, or 1,000 ml of the live yeast cells. The number of container to be taken each day to obtain the total daily dose in a subject depends on the number of activated and conditioned yeast cells contained within each container. For example, a container may comprise 50 ml of liquid with $10^7$ cells per ml and when a total daily dose of about $2\times10^9$ cells per day is desired, a subject can drink 4 containers per day to obtain the desired total daily dose.

Generally, because of their ease of administration, tablets and capsules represent the most advantageous oral dosage unit form, in which case solid pharmaceutical carriers as described above are employed. In a preferred embodiment, the composition is a capsule. The capsules can be formulated by any commercially available methods. In certain embodiments, the composition is a capsule containing 5 mg, 10 mg, 15 mg, 20 mg, 25 mg, 30 mg, 40 mg, 50 mg, 75 mg, 100 mg, 150 mg, 200 mg, 300 mg, 400 mg, 500 mg, 600 mg, 700 mg, 800 mg, 900 mg, 1.0 gram, 1.25 gram, 1.5 gram, or 2.0 gram of live yeast cells in powder form. The powder in the capsule comprises about $10^5$ to about $10^{11}$ cells per gram; more preferably, about $10^8$ to $5\times10^{10}$ cells per gram; and most preferably, about $5\times10^8$ cells per gram. The number of capsule to be taken each day to obtain the total daily dose in a subject depends on the number of activated and conditioned yeast cells contained within each capsule. For example, a capsule may comprise about 500 mg of powder with $5\times10^8$ cells per gram. To achieve a total daily dose of about $2\times10^9$ cells per day, a subject can take two capsules at a time for four times per day.

In another embodiment, the biological compositions comprising activated and conditioned yeast cells can be added directly to foods so that an effective amount of yeast cells is ingested during normal meals. Any methods known to those skilled in the art may be used to add to or incorporate the biological compositions into natural or processed foods, provided that the activated and conditioned yeast cells remain viable. Preferably, the nutritional compositions of the invention are made and stored under conditions, such as temperature, from about 0° C. to 4° C. As used herein, the term "food" broadly refers to any kind of material, liquid or solid, that is used for nourishing an animal, and for sustaining normal or accelerated growth of an animal including humans. Many types of food products or beverages, such as but not limited to, fruit juice, herbal extracts, tea-based beverages, dairy products, soybean product (e.g., tofu), and rice products, can be used to form nutritional compositions comprising the activated and conditioned yeast cells of the invention.

The invention is further defined by reference to the following example describing in detail the animal trials conducted to study the efficacy and safety of activated and conditioned yeast cells of the invention.

EXAMPLE

The following example illustrates the benefit of a biological composition of the invention in a Wistar rat model of human colorectal cancer. The growth of the tumor in the rats was studied.

According to numerous animal studies, dimethyl hydrazine (DMH) is a well known effective trigger of colorectal cancer in Wistar rats. Accordingly, this experiment used DMH in setting up a Wistar rat model of human colorectal cancer. Detailed description of the use of dimethyl hydrazine to induce colorectal cancer can be found in Madarnas P. et al., 1992, *Anticancer Res.* 12(1):113–7, which is incorporated herein by reference in its entirety.

The biological composition comprising $10^8$ cells per ml of activated and conditioned yeast cells of the strain *Saccharomyces cerevisiae* Hansen strain AS2.1396 was prepared by the methods described in Section 5.1 and subsections therein.

6.1 Preparation of DMH Mixture

A DMH mixture was prepared by mixing 400 mg DMH with 100 ml saline and 37 mg ethylene diamine tetraacetate (EDTA). The pH of the mixture was then adjusted to 6.5 using 0.1 N NaOH.

6.2 Animal Preparation

The animals used in the experiments were Wistar rats (obtained from the Chinese Academy of Military Medical Sciences, Beijing, China), male and female, with an average body weight of about 180 to 200 gram. The rats were injected subcutaneously with 21 mg of DMH mixture (as prepared in Section 6.1) per kg body weight once a week for 21 weeks.

6.3 Experimental Design

The rats that were fed with the DMH mixture for nine weeks were divided into 4 experimental groups of ten rats per group and one control group. The four experimental groups were triplicated (i.e., using a total of 120 rats in the experimental groups). In group 2AY, the rats received 2.0 ml of the biological composition once per day. In group NY, the rats received 2.0 ml of the untreated yeast cells once per day. In group AM, the rats were injected subcutaneously with $10^5$ units of amycin (AM) per kg body weight per day. In group 2CK1, the rats received 2.0 ml of physiological saline once per day. A fifth group of rats, group CK2, which did not receive tumor cells, was given 2.0 ml of physiological saline per day.

The rats received the biological compositions, untreated yeast cells, AM or saline on the same day as the tumor cells were transplanted. The rats in group CK2 also started receiving saline on the same day as the other four groups. The biological compositions, untreated yeast cells and saline were administered orally by a feeding tube and the AM by subcutaneous injection for 30 consecutive days. On the $31^{st}$ day from tumor inoculation, the rats were sacrificed. The weight of the rats, the weight of the colorectum, and the weight of the tumor were determined by standard techniques.

6.4 Results

Table 4 shows the differences in the body weight, the weight of the colorectum, and the weight of tumor of the rats in the various treatment and control groups.

TABLE 4

| Group | mean weight of rats and standard deviation (g) | mean weight of colorectum and standard deviation (mg) | mean weight of tumor nodules and standard deviation (mg) |
|---|---|---|---|
| AY | 207 ± 11 | 1,005 ± 21 | 107 ± 23 |
| NY | 189 ± 15 | 1,564 ± 39 | 655 ± 47 |
| AM | 202 ± 12 | 1,214 ± 32 | 304 ± 33 |
| CK1 | 187 ± 13 | 1,546 ± 37 | 626 ± 42 |
| CK2 | 197 ± 18 | 893 ± 22 | not applicable |

The rats bearing colorectal cancer cells that received 2.0 ml of the biological composition of the invention (group AY) showed the least deviation in the body weight and weight of colorectum as compared to healthy rats not injected with tumor cells (group CK2). The rats in group AY also had less tumor mass as compared to rats that did not receive treatment (group CK1) as well as the rats in group NY (2.0 ml of untreated yeast cells per day) and the rats in group AM (10$^5$ units of amycin per kg body weight per day).

EXAMPLE

The following example illustrates the benefit of a biological composition of the invention in a Wistar rat model of human colorectal cancer. The survival time of rats after tumor injection and treatment was studied.

The biological composition comprising 10$^8$ cells per ml of activated and conditioned yeast cells of the strain *Saccharomyces cerevisiae* Hansen strain AS2.1396 was prepared by the methods described in Section 5.1 and subsections therein.

7.1 Preparation of DMH Mixture

The DMH mixture was prepared in a similar manner as described in Section 6.1.

7.2 Animal Preparation

The animals were prepared in a similar manner as described in Section 6.1.

7.3 Experimental Design

The rats that were fed with the DMH mixture for nine weeks were divided into 4 experimental groups of ten rats per group and one control group. The four experimental groups were triplicated (i.e., using a total of 120 rats in the experimental groups). In group 2AY, the rats received 2.0 ml of the biological composition once per day. In group 2NY, the rats received 2.0 ml of the untreated yeast cells once per day. In group 2AM, the rats were injected subcutaneously with 10$^5$ units of amycin (AM) per kg body weight per day. In group 2CK1, the rats received 2.0 ml of physiological saline once per day. A fifth group of rats, group 2CK2, which did not receive tumor cells, was given 2.0 ml of physiological The rats received the biological compositions, untreated yeast cells, AM or saline on the same day as the tumor cells were transplanted. The rats in group 2CK2 also started receiving saline on the same day as the other four groups. The biological compositions, untreated yeast cells and saline were administered orally by a feeding tube and the AM by subcutaneous injection for 30 consecutive days. The rats were observed over 6 months from the day of tumor inoculation and survival was recorded. The weight of the rats, the weight of the colorectum, and the weight of the tumor were determined by standard techniques.

7.4 Results

Table 5 shows the number of rats in the various treatment and control group that survived the tumor injection over a period of 6 months. Each of the 30 rats in each group received 30 consecutive days of either untreated yeast cells, AM, saline or biological compositions of the invention. Table 6 shows the weight of the rats that survived and the weight of their tumors in the various treatment and control groups.

TABLE 5

Number of live animals remaining in the groups after 30 days of treatment

| Time after cessation of treatment | Group 2AY | Group 2NY | Group 2AM | Group 2CK1 | Group 2CK2 |
|---|---|---|---|---|---|
| 0 month | 30 | 30 | 30 | 28 | 30 |
| 1 month | 30 | 26 | 30 | 23 | 30 |
| 2 months | 30 | 11 | 26 | 17 | 30 |
| 3 months | 30 | 0 | 22 | 9 | 30 |

TABLE 5-continued

Number of live animals remaining in the groups after 30 days of treatment

| Time after cessation of treatment | Group 2AY | Group 2NY | Group 2AM | Group 2CK1 | Group 2CK2 |
|---|---|---|---|---|---|
| 4 months | 30 | 0 | 12 | 0 | 30 |
| 5 months | 30 | 0 | 0 | 0 | 30 |
| 6 months | 30 | 0 | 0 | 0 | 30 |

TABLE 6

| Group | mean weight of rats and standard deviation (g) | mean weight of colorectum and standard deviation (mg) | mean weight of tumor nodules and standard deviation (mg) |
|---|---|---|---|
| 2AY | 226 ± 14 | 976 ± 17 | 4.2 ± 1.2 |
| 2NY | all animals dead | all animals dead | all animals dead |
| 2AM | all animals dead | all animals dead | all animals dead |
| 2CK1 | all animals dead | all animals dead | all animals dead |
| 2CK2 | 228 ± 17 | 917 ± 21 | not applicable |

The rats bearing colorectal cancer cells that received 2.0 ml of the biological composition of the invention (group 2AY) survived for more than 6 months and the tumor never reoccurred. On the contrary, the rats in group 2NY (2.0 ml of untreated yeast cells per day), group 2AM (10$^5$ units of amycin per kg body weight per day) and group 2CK1 (1.2 ml of saline per day) all died after five months from injection of tumor cells.

As in Example 6, the rats bearing colorectal cancer cells that received 1.2 ml of the biological composition of the invention (group 2AY) showed the least deviation in the weight of rats as compared to healthy rats not injected with tumor cells (group 2CK2).

EXAMPLE

The following example illustrates the benefit of a biological composition of the invention in a BALB/c mouse model of human colorectal cancer. The growth of transplanted tumors in the mice was studied.

Numerous animal studies have reported the use of BALB/c mouse models in the study of human colorectal cancer. There is almost a 100% success rate for transplanting colorectal tumor Ca-26 cells in mice.

The biological composition comprising 10$^8$ cells per ml of activated and conditioned yeast cells of the strain *Saccharomyces cerevisiae* Hansen strain AS2.1396 was prepared by the methods described in Section 5.1 and subsections therein.

8.1 Animal Preparation

The animals used for the experiments were BALB/c mice (obtainable from the Chinese Academy of Military Medical Sciences, Beijing, China), 6 to 8 weeks old. Both males and females with average body weight of about 15 to 18 gram were used. About 10$^6$ viable tumor cells of the colorectal cancer cell line Ca-26 (about 0.2 ml culture suspension) were injected subcutaneously into the animals.

8.2 Experimental Design

The mice injected with tumor cells were kept for 5 days and then divided into 4 experimental groups of ten mice per group and one control group. The four experimental groups were triplicated (i.e., using a total of 120 mice in the experimental groups). In group AY, the mice received 0.3 ml of the biological composition once per day. In group NY, the mice received 0.3 ml of the untreated yeast cells once per day. In group AM, the mice were injected subcutaneously with $10^5$ units of amycin (AM) per kg body weight per day. In group CK1, the mice received 0.3 ml of physiological saline once per day. A fifth group of mice, group CK2, which did not receive tumor cells, was given 0.3 ml of physiological saline per day.

The mice received the biological compositions, untreated yeast cells, AM or saline on the same day as the tumor cells were transplanted. The mice in group CK2 also started receiving saline on the same day as the other four groups. The biological compositions, untreated yeast cells and saline were administered orally by a feeding tube and the AM by subcutaneous injection for 30 consecutive days. On the $31^{st}$ day from tumor inoculation, the mice were sacrificed and the weight of the mice, the weight of the colorectum, and the weight of the tumor were determined by standard techniques.

8.3 Results

Table 7 shows the differences in the body weight, the weight of the colorectum, and the weight of tumor of the mice in the various treatment and control groups.

TABLE 7

| Group | mean weight of mice and standard deviation (g) | mean weight of colorectum and standard deviation (mg) | mean weight of tumor nodules and standard deviation (mg) |
| --- | --- | --- | --- |
| 2AY | 17.7 ± 2.0 | 379 ± 17 | 69 ± 13 |
| 2NY | 17.3 ± 1.3 | 641 ± 29 | 277 ± 27 |
| 2AM | 17.4 ± 1.5 | 587 ± 23 | 247 ± 29 |
| 2CK1 | 16.5 ± 1.7 | 623 ± 31 | 286 ± 33 |
| 2CK2 | 17.8 ± 2.1 | 326 ± 14 | not applicable |

The mice bearing colorectal cancer cells that received 0.3 ml of the biological composition of the invention (group AY) showed the least deviation in the weight of mice as compared to healthy mice not injected tumor cells (group CK2). The mice in group AY also had less tumor mass as compared to mice that did not receive treatment (group CK1) as well as the mice in group NY (0.3 ml of untreated yeast cells per day) and the mice in group AM ($10^5$ units of amycin per kg body weight per day).

EXAMPLE

The following example illustrates the benefit of a biological composition of the invention in a BALB/c mouse model of human colorectal cancer. The survival time of mice after tumor injection and treatment was studied.

The biological composition comprising $10^8$ cells per ml of activated and conditioned yeast cells of the strain *Saccharomyces cerevisiae* Hansen strain AS2.1396 was prepared by the methods described in Section 5.1 and subsections therein.

9.1 Animal Preparation

The animals were prepared in a similar manner as described in Section 8.1.

9.2 Experimental Design

The mice injected with tumor cells were kept for 5 days and then divided into 4 experimental groups of ten mice per group and one control group. The four experimental groups were triplicated (i.e., using a total of 120 mice in the experimental groups). In group 2AY, the mice received 0.3 ml of the biological composition once per day. In group 2NY, the mice received 0.3 ml of the untreated yeast cells once per day. In group 2AM, the mice were injected subcutaneously with $10^5$ units of amycin (AM) per kg body weight per day. In group 2CK1, the mice received 0.3 ml of physiological saline once per day. A fifth group of mice, group 2CK2, which did not receive tumor cells were given 0.3 ml of physiological saline per day.

The mice received the biological compositions, untreated yeast cells, AM or saline on the same day as the tumor cells were transplanted. The mice in group CK2 also started receiving saline on the same day as the other four groups. The biological compositions, untreated yeast cells and saline were administered orally by a feeding tube and the AM by subcutaneous injection for 30 consecutive days. The mice were observed over 6 months from the day of tumor inoculation and survival was recorded. The weight of the mice, the weight of the colorectum, and the weight of the tumor were determined by standard techniques.

9.3 Results

Table 8 shows the number of mice in the various treatment and control group that survived the tumor injection over a period of 6 months. Each of the 30 mice in each group received 30 consecutive days of either untreated yeast cells, AM, saline or biological compositions of the invention. Table 9 shows the weight of the mice that survived and the weight of their tumors in the various treatment and control groups.

TABLE 8

Number of live animals remaining in the groups after 30 days of treatment

| Time after cessation of treatment | Group 2AY | Group 2NY | Group 2AM | Group 2CK1 | Group 2CK2 |
| --- | --- | --- | --- | --- | --- |
| 0 month | 30 | 29 | 30 | 30 | 30 |
| 1 month | 30 | 23 | 30 | 27 | 30 |
| 2 months | 30 | 0 | 27 | 0 | 30 |
| 3 months | 30 | 0 | 21 | 0 | 30 |
| 4 months | 30 | 0 | 0 | 0 | 30 |
| 5 months | 30 | 0 | 0 | 0 | 30 |
| 6 months | 30 | 0 | 0 | 0 | 30 |

TABLE 9

| Group | mean weight of rats and standard deviation (g) | mean weight of colorectum and standard deviation (mg) | mean weight of tumor nodules and standard deviation (mg) |
| --- | --- | --- | --- |
| 2AY | 18.4 ± 1.4 | 354 ± 16 | 23.6 ± 0.9 |
| 2NY | all animals dead | all animals dead | all animals dead |
| 2AM | all animals dead | all animals dead | all animals dead |
| 2CK1 | all animals dead | all animals dead | all animals dead |
| 2CK2 | 18.7 ± 1.2 | 347 ± 19 | not applicable |

The mice bearing colorectal cancer cells that received 0.3 ml of the biological composition of the invention (group 2AY) survived for more than 6 months and the tumor never reoccurred. On the contrary, the mice in group 2NY (0.3 ml of untreated yeast cells per day), group 2AM ($10^5$ units of amycin per kg body weight per day) and group CK1 (0.3 ml of saline per day) all died after four months from injection of tumor cells.

As in Example 7, the mice bearing colorectal cancer cells that received 0.3 ml of the biological composition of the invention (group 2AY) showed the least deviation in the weight of mice as compared to healthy mice not injected with tumor cells (group 2CK2).

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein, will become apparent to those skilled in the art from the foregoing description and accompanying drawings. Such modifications are intended to fall within the scope of the appended claims.

All publications, patents and patent applications mentioned in this specification are herein incorporated by reference into the specification to the same extent as if each individual publication, patent or patent application was specifically and individually indicated to be incorporated herein by reference.

What is claimed is:

1. A biological composition comprising activated yeast cells, wherein said activated yeast cells are cells of *Saccharomyces cerevisiae* Hansen strain AS2.1396 and are characterized by their ability to retard the growth of colorectal cancer cells in mammals as compared to yeast cells of said strain not having been so activated, wherein said activated yeast cells are prepared by using yeast cells of *Saccharomyces cerevisiae* Hansen strain AS2.1396 in a method comprising at least two steps selected from the group consisting of:
   (a) culturing said yeast cells in a first electromagnetic field having a frequency in the range of 7,941 to 7,950 MHz and a field strength in the range of 230 to 250 mV/cm;
   (b) culturing said yeast cells in a second electromagnetic field having a frequency in the range of 9,131 to 9,140 MHz and a field strength in the range of 220 to 240 mV/cm;
   (C) culturing said yeast cells in a third electromagnetic field having a frequency in the range of 9,991 to 10,000 MHz and a field strength in the range of 250 to 270 mV/cm;
   (d) culturing said yeast cells in a fourth electromagnetic field having a frequency in the range of 11,141 to 11,150 MHz and a field strength in the range of 230 to 250 mV/cm; and
   (e) culturing said yeast cells in a fifth electromagnetic field having a frequency in the range of 12,771 to 12,780 MHz and a field strength in the range of 260 to 280 mV/cm.

2. The biological composition of claim 1, wherein the activated yeast cells are at a concentration of about $10^6$ to $10^9$ cells per ml.

3. The biological composition of claim 1, wherein the activated yeast cells are dried and at a concentration of about $10^7$ to $10^{10}$ cells per gram.

4. A method for preparing a biological composition comprising activated yeast cells, wherein said activated yeast cells are cells of *Saccharomyces cerevisiae* Hansen strain AS2.1396 and are characterized by their ability to retard the growth of colorectal cancer cells in mammals as compared to yeast cells of said strain not having been so activated, said method comprising providing yeast cells of *Saccharomyces cerevisiae* Hansen strain AS2.1396, and at least two steps selected from the group consisting of:
   (a) culturing said yeast cells in a first electromagnetic field having a frequency in the range of 7,941 to 7,950 MHz and a field strength in the range of 230 to 250 mV/cm;
   (b) culturing said yeast cells in a second electromagnetic field having a frequency in the range of 9,131 to 9,140 MHz and a field strength in the range of 220 to 240 mV/cm;
   (C) culturing said yeast cells in a third electromagnetic field having a frequency in the range of 9,991 to 10,000 MHz and a field strength in the range of 250 to 270 mV/cm;
   (d) culturing said yeast cells in a fourth electromagnetic field having a frequency in the range of 11,141 to 11,150 MHz and a field strength in the range of 230 to 250 mV/cm; and
   (e) culturing said yeast cells in a fifth electromagnetic field having a frequency in the range of 12,771 to 12,780 MHz and a field strength in the range of 260 to 280 mV/cm.

* * * * *

UNITED STATES PATENT AND TRADEMARK OFFICE
CERTIFICATE OF CORRECTION

PATENT NO. : 7,163,813 B2 Page 1 of 1
APPLICATION NO. : 11/226673
DATED : January 16, 2007
INVENTOR(S) : Ling Yuk Cheung It is certified that error appears in the above-identified patent and that said Letters Patent is hereby corrected as shown below:

Column 3, line 31, the term "Malkion" should read --Malkinson--;

Column 20, line 24, the expression "2AY" should read --AY--;

Column 20, line 29, the expression "2CK1" should read --CK1--; and

Column 21, line 34, after the word "physiological," insert the expression --saline once per day--.

Signed and Sealed this

Twenty-fourth Day of April, 2007

JON W. DUDAS
*Director of the United States Patent and Trademark Office*